US007098353B2

(12) United States Patent
Zhang et al.

(10) Patent No.: US 7,098,353 B2
(45) Date of Patent: Aug. 29, 2006

(54) METAL ION EXCHANGED SOLID MATERIALS AS CATALYSTS FOR THE SKELETAL ISOMERIZATION OF FATTY ACIDS AND ALKYL ESTERS THEREOF

(75) Inventors: Zongchao Zhang, Norwood, NJ (US); Shuguang Zhang, New Rochelle, NY (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/412,201

(22) Filed: Apr. 11, 2003

(65) Prior Publication Data

US 2004/0204598 A1    Oct. 14, 2004

(51) Int. Cl.
*C07C 51/00* (2006.01)
(52) U.S. Cl. ............... 554/158; 554/128; 554/141; 554/145; 502/77; 502/78
(58) Field of Classification Search ............... 554/158, 554/128, 141, 145; 502/77, 78
See application file for complete search history.

(56) References Cited

U.S. PATENT DOCUMENTS

| 5,364,949 A | 11/1994 | Neuss et al. ............... 554/161 |
| 5,677,473 A | 10/1997 | Tomifuji et al. ............ 554/158 |
| 5,856,539 A | 1/1999 | Hodgson et al. ............ 554/125 |
| 6,455,716 B1 * | 9/2002 | Kenneally et al. .......... 554/158 |

FOREIGN PATENT DOCUMENTS

| WO | WO01/66507 A2 | 9/2001 |
| WO | WO01/66507 A3 | 9/2001 |
| WO | WO03/006157 A2 | 1/2003 |
| WO | WO03/006157 A3 | 1/2003 |

OTHER PUBLICATIONS

"Location, Ligancy and Reducibility of Metal Ions in Zeolites Cages: Co and Pd in NaY", Z. Zhang, and W.M.H. Sachtler, J. Chem. Soc. Faraday Trans., 86 (1990) pp. 2313-2319.

* cited by examiner

*Primary Examiner*—Deborah D. Carr
(74) *Attorney, Agent, or Firm*—Ralph J. Mancini

(57) ABSTRACT

The present invention generally relates to a process for the skeletal isomerization of unsaturated linear fatty acids and/or alkyl esters thereof to their branched counterparts. Said skeletal isomerization process comprises contacting said unsaturated linear fatty acids and/or alkyl esters thereof with at least one metal ion exchanged solid material catalyst. The present invention also relates to a process for the preparation of branched fatty acids and/or alkyl esters thereof from their straight chain counterparts. Finally, the invention also relates to various derivatives prepared from the branched fatty acids and/or alkyl esters prepared in accordance with the present invention.

38 Claims, 5 Drawing Sheets

Figure 2:
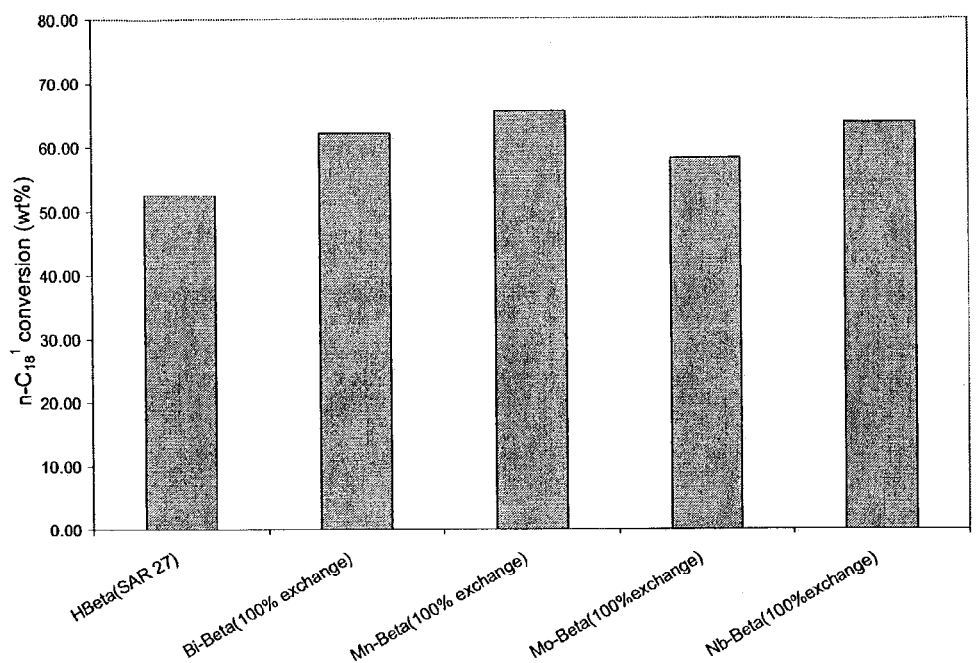

Figure 2 High throughput screening of zeolites exchanged with different cations.

METAL ION EXCHANGED SOLID MATERIALS AS CATALYSTS FOR THE SKELETAL ISOMERIZATION OF FATTY ACIDS AND ALKYL ESTERS THEREOF

This application hereby claims benefit of prior, copending, non-provisional application Ser. No. 10/177,405 filed on Jun. 2, 2002.

FIELD OF THE INVENTION

The present invention generally relates to metal ion exchanged solid materials as catalysts and to the use of said catalysts for the isomerization of fatty acids and/or alkyl esters thereof. The invention also relates to the branched acids and alkyl esters prepared by the aforementioned process, and derivatives prepared therefrom.

BACKGROUND OF THE INVENTION

Fatty acids and alkyl esters thereof are the building blocks for various compositions ranging from lubricants, polymers, solvents, cosmetics and the like. Fatty acids are generally obtained by hydrolysis of triglycerides of vegetable or animal origin. Naturally occurring triglycerides are esters of glycerol and generally straight chain, even numbered carboxylic acids, in size ranging from 10–24 carbon atoms. Most common are fatty acids having 12, 14, 16 or 18 carbon atoms. The fatty acids are either saturated or contain one or more unsaturated bonds.

Long, straight chain saturated fatty acids (C10:0 and higher) are solid at room temperature, which makes them difficult to process in a number of applications. Unsaturated long chain fatty acids, however, e.g. oleic acid are liquid at room temperature, so are easy to process, but are unstable because of the existence of double bond(s). Branched fatty acids mimic the properties of the straight chain unsaturated fatty acids in many respects, but do not have the disadvantage of being unstable. "Branched fatty acids" means fatty acids containing one or more alkyl side groups, and/or aryl groups, which are attached to the carbon chain backbone at any position. Therefore, branched fatty acids are for many applications more desirable than straight chain fatty acids. Commercial branched acids are not, however, naturally occurring materials.

Currently, branched fatty acids are obtained by isomerization (branching) of the straight chain, unsaturated fatty acids having a corresponding chain length. For example, branched C18:0 is prepared from straight C18:1 (or also C18:2). Various routes are known for said isomerization or branching of fatty acids in the art.

In one process, for example, clay is used as a catalyst. Clay catalyzed isomerization suffers, however, from two main disadvantages. First, a considerable amount of undesired side products containing oligomers, saturated straight chain fatty acids and intermediate dimers is formed. A second disadvantage is that the clay catalyst cannot be reused.

U.S. Pat. No. 5,856,539 discloses an isomerization process whereby a fatty acid feed comprising unsaturated fatty acids is contacted with a catalyst, characterized in that the catalyst comprises a material having a microporous structure.

U.S. Pat. No. 5,677,473 describes a process for preparing branched chain fatty acids or alkyl esters thereof which comprises subjecting unsaturated fatty acids having 10–25 carbon atoms or alkyl esters thereof to a skeletal isomerization reaction in the presence of water or a lower alcohol using a zeolite as a catalyst. The zeolite has a linear pore structure of a size small enough to retard dimerization and large enough to allow diffusion of the branched fatty acids or alkyl esters thereof.

U.S. Pat. No. 5,364,949 describes a process for the production of branched fatty acids and their esters, which comprises reacting unsaturated fatty acids or esters thereof with aliphatic nonactivated olefins in the presence of layer silicates and active carbon.

However, all of these processes are plagued by low yield and/or a high rate of undesireable byproduct formation. Accordingly, there is a need for a new process that overcomes these disadvantages, i.e. a process for the preparation of branched fatty acids from straight chain unsaturated fatty acid feedstocks with a high conversion rate, an increased selectivity towards branched monomeric isomers and which employs a reusable catalyst.

SUMMARY OF THE INVENTION

The present invention generally relates to a process for the skeletal isomerization of unsaturated linear fatty acids and/or alkyl esters thereof to their branched counterparts. Said process comprises contacting said unsaturated linear fatty acids and/or alkyl esters thereof with at least one metal ion exchanged solid material catalyst. The present invention also relates to a process for the preparation of branched fatty acids and/or alkyl esters thereof from their straight chain counterparts. Finally, the invention also relates to various derivatives prepared from the branched fatty acids and/or alkyl esters prepared in accordance with the present invention.

DETAILED DESCRIPTION OF THE PRESENT INVENTION

In the context of the present invention the inventors have discovered that metal ion exchanged zeolites are highly active for catalyzing reactions of feedstocks comprising carboxylic acids. The catalyzed reactions include, but are not limited to, isomerizations, alkylations, and the like. The feedstock comprises carboxylic acids, including but not limited to aliphatic and/or aromatic carboxylic acids. A preferred feedstock comprises fatty acids or esters thereof.

In one embodiment the present invention relates to a process for the skeletal isomerization of unsaturated linear fatty acids and/or alkyl esters to their branched counterparts. The process comprises contacting said unsaturated linear fatty acids and/or methyl esters thereof with at least one metal ion exchanged solid material catalyst. The catalyst and process of the invention advantageously converts fatty acid and/or alkyl ester feedstock into a mixture that is rich in branched fatty acids and/or branched alkyl esters and low in oligomers. While the reaction products of the present process will generally comprise both saturated as well as unsaturated products, both are thus included in the invention, there is high selectivity towards the formation of branched fatty acids and/or alkyl esters.

The invention also relates to various derivatives prepared from the branched fatty acids and/or alkyl esters prepared in accordance with the present invention.

The catalyst of the invention is characterized in that it is a metal ion exchanged material comprising zeolites, clays, resins, amorphous oxides, molecular sieves or their mixtures. The metal ions can be from a single metal or from multiple metals, with or without other additives. The sources of metal ions can be from any salts containing the metal ions with or without ligands. Mixed metal ions or their complexes with various ligands can be used. Ion exchange can be carried out in an aqueous phase, or in the absence of aqueous phase, e.g. solid state exchange by physically mixing the solid materials with one or more metal ion containing salts followed by calcination at elevated temperature. The ion exchange level can range from trace metal ions to 100% metal ion level based on ion exchange capacity. Over exchange to a level about 100% of ion exchange capacity can also result in active catalysts. It is known that certain noble metal ions, such as $Pt^{2+}$ and $Pd^{2+}$, in zeolites can be reduced by hydrogen at temperatures above 120° C. Even though most metal oxides can be readily reduced by hydrogen at temperatures of about 350° C., the reduction of most transition metal ions in zeolites by hydrogen generally requires much higher temperature. See *Location, Ligancy and Reducibility of Metal Ions in Zeolites: Co and Pd in NaY*, Z. Zhang, and W. M. H. Sachtler, *J. Chem. Soc. Faraday Trans.*, 86 (1990) 2313, which is incorporated herein by reference. This invention relates to a process in which hydrogen is preferably not used. However, for non-reducible metal ions, use of hydrogen is not harmful to the product yield.

As an example, acidic proton form ($H^+$) zeolites, such as HZSM-5, H-Mordenite, HBeta, and HY, are known to be active for the isomerization of unsaturated fatty acids to branched fatty acids. Proton form zeolites containing group VIII zero valent metals are also active catalysts as zero valent metals do not affect the overall proton concentrations in zeolites. When positively charged protons are replaced by metal ions, the overall proton concentrations decrease. As isomerization is known to typically take place via protonated carbenium ion mechanism, the concentration and strength of proton acidity are critical for skeletal isomerization activity of proton form zeolites.

In a preferred mode the invention contemplates the skeletal isomerization of unsaturated fatty acids, even at near or over 100% ion exchange. This is particularly unexpected based on conventional wisdom as the concentration of protons is significantly reduced if not completely eliminated. It is preferred that higher valent metals be employed in the catalysts of the claimed invention. By higher valent metals it is meant that the valency of the metal(s) must be greater than zero. Most divalent and trivalent metal ions from the periodic table showed improved catalytic activity over purely proton form zeolites toward the isomerization and aryl branching of unsaturated fatty acids. The activity varies with the type of cation and the degree of ion exchange.

Examples of higher valent metals that can be exchanged on the catalyst of the claimed invention include, but are not limited to: $Li^+$, $Cu^+$, $Rh^+$, $Ir^+$, $Mg^{2+}$, $Ca^{2+}$, $Mn^{2+}$, $Fe^{2+}$, $Co^{2+}$, $Ni^{2+}$, $Cu^{2+}$, $Zn^{2+}$, $Sr^{2+}$, $Mo^{2+}$, $Pd^{2+}$, $Sn^{2+}$, $Ce^{2+}$, $Pt^{2+}$, $Sc^{3+}$, $Cr^{3+}$, $Fe^{3+}$, $Co^{3+}$, $Ga^{3+}$, $Y^{3+}$, $Nb^{3+}$, $Ru^{3+}$, $Rh^{3+}$, $La^{3+}$, $Ln^{3+}$ and the rest of the rare earth elements, $Ir^{3+}$, $Bi^{3+}$, $Ti^{4+}$, $Mn^{4+}$, $Zr^{4+}$, $Mo^{4+}$, $Sn^{4+}$, $Ce^{4+}$, $V^{5+}$, $Nb^{5+}$, $Mo^{6+}$, mixtures thereof and the like.

In a preferred embodiment the metal ion concentration of the catalyst employed is at least 0.001% of the exchange capacity. In another embodiment the metal ion concentration is at least 0.5% of the exchange capacity. In still another embodiment the metal ion concentration is at least 1% of the exchange capacity. In yet another embodiment the metal ion concentration is at least 2% of the exchange capacity. In most embodiments of the invention it is preferred that the metal ion concentration is said catalyst is in the range of 0.001 to above 200% exchange level; preferably in the range of 0.5 to 200% exchange level. In another embodiment the metal ion concentration is in the range of 0.5 to 100% exchange level. In still another embodiment the metal ion concentration is in the range of 1 to 50% exchange level.

The metal ion exchanged acid catalyst of the invention can be used alone or in mixtures with one or more solid materials.

Various acidic catalysts are known to the skilled artisan. Examples of acidic catalysts employable in the claimed process include but are not limited to zeolites, acidic clays, molecular sieves and the like.

Zeolites are crystalline aluminosilicates generally represented by the formula

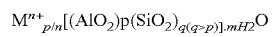

where M is a metal cation of groups IA including Hydrogen or IIA and n is the valency of this metal. Zeolites consist of a network of $SiO_4$ and $AlO_4$ tetrahedra linked together via shared oxygen atoms. Aluminum has a $3^+$ valency resulting in an excess negative charge on the $AlO_4$ tetrahedra, which can be compensated by cations such as $H^+$. When M is hydrogen the materials are Bronsted acidic, when M is for example Cs the materials are basic. Upon heating, Bronsted acidic hydroxyls dehydrate creating coordinately unsaturated Al, which acts as a Lewis acid site. The acid strength, acid site density and Bronsted versus Lewis acidity are determined by the level of framework aluminum. The ratio of silica/alumina can be varied for a given class of zeolites either by controlled calcination, with or without the presence of steam, optionally followed by extraction of the resulting extra framework aluminum or by chemical treatment employing for example ammonium hexafluorosilicate.

As zeolite frameworks are typically negatively charged, the charge balancing cations related to this invention include monovalent cations such as $H^+$, $Li^+$ and the like, divalent cations such as $Mg^{2+}$, $Zn^{2+}$ and the like and trivalent cations such as $Ln^{3+}$, $Y^{3+}$, $Fe^{3+}$, $Cr^{3+}$ and the like. The framework composition of the three-dimensional zeolites may contain other elements in addition to Al and Si, such as, for example, P, Ti, Zr, Mn, and the like. Although any zeolite meeting the parameters of this embodiment of the present invention can be employed, faujasite (e.g. Y zeolite), Beta zeolite, Offeretite and the like are particularly well suited for the present process. The Si/Al ratio of the zeolites can vary depending on the particular zeolite employed provided that the skilled artisan understands that a ratio which is too low will result in more by-products and a ratio which is too high will lower the activity of the zeolite. In most cases the Si/Al ratio of the zeolites is at least 2, up to at least 20 and higher. For example, the Si/Al ratio for Beta zeolite may be from about 5–75 while that for Y zeolite can be from 2 to about 80.

The present invention is not limited to zeolites in general, or to a particular zeolite, as materials other than zeolites can be employed in the context of the present invention. Zeolites are, however, a preferred material to be employed and the use of any known or yet to be discovered zeolites is included within the scope of the present invention. Examples of zeolites which can be employed in the context of the present invention include, but are not limited to, zeolite A, Beta zeolite, zeolite X, zeolite Y, zeolite L, zeolite ZK-5, zeolite ZK-4, zeolite ZSM-5, zeolite ZSM-11, zeolite ZSM-12, zeolite ZSM-20, ZSM-35, zeolite ZSM-23, aluminophosphates including but not limited to VPI-5 and the like, and mixtures thereof, and/or zeolitic materials having the following framework structures: AEL, AFO, AHT, BOG, CGF, CGS, CON, DFO, FAU, FER, HEU, AFS, AFY, BEA, BPH, CLO, EMT, FAU, GME, MOR, MFI, and the like.

Good selectivity and conversion can be obtained by the process of the present invention if at least part of the isomerization is performed at a temperature of between about 100° C. and 350° C. In another embodiment, the process of the invention is performed at a temperature of between about 230° C. and 285° C. Since the conversion is also a function of the reaction/contact time, it is preferred that the fatty acid feedstock is contacted with the catalyst for a period of at least 5 minutes and reaction times of 1–16 hours are typical. An even longer period could be used if the process is operated at a lower temperature.

In general, the amount of catalyst employed in the process according to the invention is between 0.01 and 30% by weight when the process is carried out in batch or semi-batch process, based on the total reaction mixture. In another embodiment the amount of catalyst used between 0.5 and 10% by weight. In still another embodiment the catalyst amounts are between 1 and 5% by weight.

The processes of the present invention can be performed both in batch and fixed bed continuous processes. Good selectivity and conversion can be obtained by the process of the present invention if at least part of the isomerization is performed at a temperature of between about 100° C. and 350° C. In another embodiment, the process of the invention is performed at a temperature of between about 230° C. and 285° C. Since the conversion is also a function of the reaction/contact time, it is preferred that the feedstock is contacted with the catalyst for a period of at least 5 minutes and reaction times of 1–16 hours are typical. An even longer period could be used if the process is operated at a lower temperature.

In general, the amount of catalyst employed in the process according to the invention is between 0.015 and 2030% by weight, based on the total reaction mixture. In another embodiment the amount of catalyst used between 0.5 and 10% by weight. In still another embodiment the catalyst amounts are between 1 and 5% by weight.

When a continuous flow reactor is employed, the weight hour space velocity is between 0.01 and 25100. Weight hour space velocity is defined as the weight of feed in grams passing over one gram of catalyst per hour.

Additionally, it has been found that by using a catalyst system according to this invention it is possible to reuse the catalyst. In some cases it may be desired to add fresh catalyst while optionally removing a part of the spent catalyst, and in other cases regeneration of the catalyst may be desired. Regeneration can be effected by various methods know to the skilled artisan. For example, regeneration can be accomplished by utilizing controlled oxidative regeneration and/or by washing with a solvent.

Typical feedstocks comprise carboxylic acids. A preferred feedstock comprises fatty acids and esters derived from natural fats and oils. Such feedstocks are predominantly unsaturated linear alkylcarboxylic acids, related esters or mixtures thereof, optionally containing other organics. Since the present process is designed for isomerization or conversion of unsaturated fatty acids and/or alkyl esters into their branched counterparts, it is beneficial if the comprises of at least about 30% by weight of said unsaturated fatty acids and/or alkyl esters. In another embodiment, the feedstock comprises at least 50% by weight of unsaturated fatty acids and/or alkyl esters. Any unsaturated and/or polyunsaturated fatty acid and/or alkyl esters, or mixtures thereof is suitable as a feedstock in accordance with the present invention. In one embodiment, the feedstock comprises oleic acid as the unsaturated fatty acid and/or the alkyl ester of oleic acid in an amount of at least 40% by weight, preferably at least 70% by weight.

The invention also relates to the branched fatty acids and alkyl esters prepared by the processes described herein. More particularly, as evidenced by the examples hereinafter provided, the process of the present invention allows one to prepare branched fatty acids having unique branching characteristics. In this regard the present inventors have tested commercially available branched fatty acids and have determined that the ratio of di-branching to mono-branching in such products is below 0.75, while that ratio for products of the present invention is above 0.75. This is clearly demonstrated in example 7 of the present application. By mono-branching it is meant that the said fatty acid has one side branch; di-branching means two side branches, etc.

In view of the novel character of the products produced in accordance with the present invention, the inventors claim isomerized products having a di-branching:mono-branching ratio of greater than 0.75. In another embodiment the inventors claim isomerized products having a di-branching:mono-branching ratio of greater than 0.80. In still another embodiment applicants claim isomerized products having a di-branching:mono-branching ratio of greater than 0.85. In yet another embodiment isomerized products having a di-branching:mono-branching ratio of greater than 0.90 are claimed. In still yet another embodiment isomerized products having a di-branching:mono-branching ratio of greater than 0.75 up to about 3.5; preferably 0.8 to 3.5, in another embodiment 0.9 to 3.0, and in yet another embodiment greater than 1.0 are claimed Additionally, in the commercial products analyzed the ratio of total (Di-+multi-) branched/mono-branched in the commercial products was found to be 1 or below, while the ratio for the isomerized products of the present invention is above 1.20. Therefore, isomerized products according to the invention having a ratio of total (Di-+multi-) branched/mono-branched above 1.20 are part of the claimed invention.

The invention also contemplates all derivatives prepared from branched fatty acids and alkyl esters thereof of the present invention.

Fatty acid alkyl esters and fatty acids are versatile building blocks and conversion of these materials into a wide variety of other surfactants is possible. Some examples of the type of reactions possible are listed below. From these starting materials it is possible to produce non-ionic, anionic and cationic surfactants, all of which is within the scope of the present invention.

The branched fatty acid alkyl esters and fatty acids products of the present invention can be utilized as starting materials to prepare the same derivatives as their linear counterparts. For example, the branched alkyl esters of the present invention are readily converted into fatty acid glucamides and glycerol esters. Alkylation of polyhydridic molecules is possible. An example of this type of reaction would be reaction of a branched methyl ester with sucrose to prepare sucrose esters. Conversion of branched alkyl esters to alpha sulfonates is known. For example, branched fatty acid ester sulfonates (FAES) can be produced from branched methyl esters by sulfonation, followed by bleaching and neutralization. Branched fatty acid alkyl esters can also be converted into other branched alkyl esters by a transesterification reaction. In most cases, the smaller molecular weight alcohol is removed from the reaction mixture forcing the reaction to the desired products.

Branched fatty acids undergo many of the same reactions their linear counterparts as well as linear and branched fatty acid alkyl esters. For example, the branched fatty acid of the present invention may be converted into its' soap form by neutralization with a base. N-acyl sarcosinates can be prepared from reaction of the branched fatty acid of the present invention fatty acid or its derivatives with sarcosine. Acylated protein hydrolysates are prepared by acylation of protein hydrolysates with branched fatty acids or acid chlorides. The hydrolysates are variable in composition, depending on how they are prepared. These are mild surfactants used in often in personal care formulations. 2-Sulfoethyl esters of branched fatty acids, also known as acyl isethionates, are excellent surfactants. This family tends to be mild to the skin and hard water tolerant. Amido propyl amine and derivatives are prepared from the fatty acid or fatty acid alkyl ester. This family of surfactants has seen commercial application in laundry detergents, dishwashing liquids and many personal care formulations. Condensation of a fatty acid alkyl ester or fatty acid with an alkanolamine results in the formation of an alkanolamide. The alkanolamide and it derivatives have a variety of uses commercially depending on its specific chemical structure. Ethoxylated alkanolamides are used as compatibilizers in formulations. Many alkanolamides and derivatives are used as thickeners and foamers. Branched fatty acids can be alkoxylated with ethylene oxide, propylene oxide and butylenes oxide to make a useful family of non-ionic surfactants. Branched fatty acids can be converted into nitriles which are the building blocks for a large variety of cationic and amine surfactants. Branched fatty acids can also be used in a reaction to prepare esteramines, which are quaternized, esterquats. The major use of esterquats is in household fabric softeners.

Conversion of the branched alkyl esters and branched fatty acids into branched alcohols can also be done. The alcohol is another building block to prepare other types of surfactants. Alcohols are used to prepare alkyl polyglycosides (APGs). These materials offer a hydrophile based on a natural sugar. Conversion of the alcohol into amines and quaternaries occurs readily and is a commercially important reaction in the preparation of cationic surfactants. Nonionic surfactants are prepared by alkoxylation of alcohols. Common alkoxylation agents are ethylene oxide, propylene oxide and butylene oxide. Conversion of alcohols (with or without alkoxylation) to alcohol sulfates is a commercially important process. The use of alcohol sulfates in laundry is increasing especially in Europe. Other areas of use include shampoos, textile processing and emulsion polymerization. Alcohols can also be converted in phosphate esters. Both mono and di phosphate esters can be favored depending on the reaction conditions. Polyalkoxycarbonates are produced by the reaction of sodium chloroacetate with an alcohol ethoxylate, or from acrylic acid and an alcohol ethoxylate. These can also be made by direct oxidation of the alcohol ethoxylate under carefully controlled conditions.

The aforementioned description is merely illustrative and not intended to limit the scope of the invention. Accordingly, one of ordinary skill in the art would readily recognize that the branched products of the present invention, like their linear counterparts, can be readily employed as starting materials in the preparation of numerous derivatives as illustrated by the following chart. Any and all of the derivatives prepared from the novel products of the present invention are within the scope of the present invention.

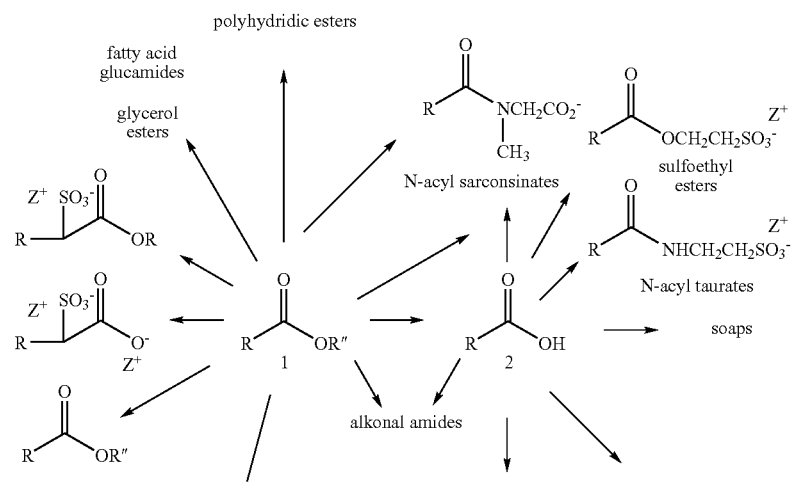

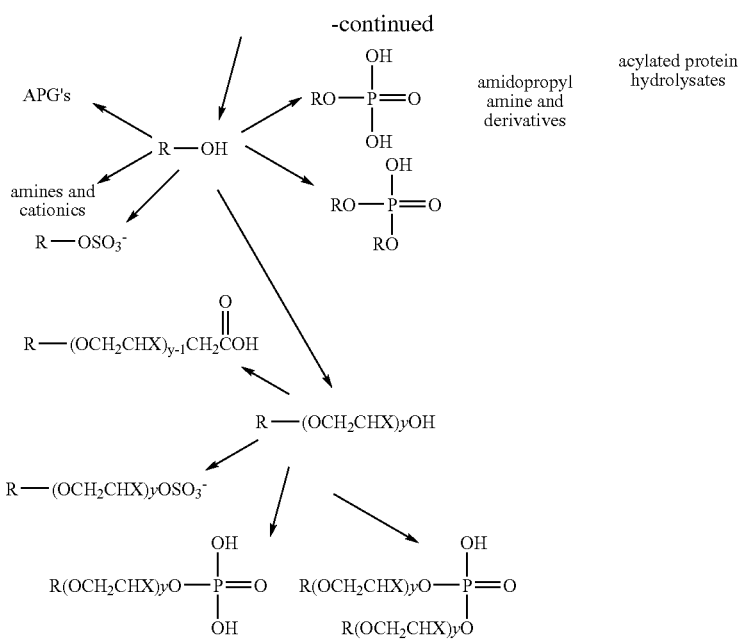

The invention will be illustrated by the following non-limiting examples.

Ion-Exchange Procedure

Two general procedures for ion-exchange have been employed to prepared metal ion exchanged zeolites: aqueous ion-exchange and solid state ion-exchange.

Aqueous Procedure

To conduct aqueous ion-exchange, a calculated amount of metal salt, for example $Cu(NO_3)_2$ for $Cu^{2+}$ exchange, is dissolved in distilled and deionized water. Then certain amount of $NH_4^+$ form zeolite is added. The weight ratio of the water to the zeolite is about 12. The amount of metal salt added depends on how much $NH_4^+$ cations in the zeolite needs to be exchanged. For example, if 4000 g of zeolite contains 1 mol $NH_4^+$ and an exchange of 20% is desired, then 0.1 mol of $Cu^{2+}$ is needed since 1 mol $Cu^{2+}$ can replace 2 mol of $NH_4^+$. Therefore, 0.1 mol of $Cu(NO_3)_2$ will be added to 48 L water and then 4000 g of the zeolite is added. The pH of the solution is adjusted to 5 with $HNO_3$. With stirring, the whole mixture is heated to 60° C. and maintained for 24 h. The zeolite is separated from the solution by filtration and washed with distilled and deionized Water three times, 48 L water each time. The zeolite is filtered, dried at 110° C. overnight and calcined at 550° C. for 6 h in air. An excessive amount of salt can be employed to achieve high degree of exchange.

Solid Procedure

To conduct solid-state ion-exchange, a calculated amount of metal salt, such as $CuCl_2$ for $Cu^{2+}$ exchange, is mixed with dry $H^+$ form zeolite. The mixture is heated in $N_2$ to 550° C. at a rate of 0.5° C./min and maintained at 550° C. for 10 h. The amount of the salt is based on how much $H^+$ needs to be exchanged. After the calcination, the zeolite can be used directly or it can be washed with distilled and deionized water, calcined again at 500° C. for 3 h before use.

EXAMPLE 1

Fatty Acid Ester Isomerization

Two grams of $Cu^{2+}$ exchanged Beta catalyst (Si/Al=27, powder, 550° C. calcined in air) and 20 g of methyl oleate were loaded into a 135 ml autoclave reactor under nitrogen. After sealed, the reactor was purged with nitrogen. A nitrogen pressure of 50 psig was approached at room temperature. With an active stirring at 1000 RPM, the mixture of methyl oleate and the catalyst was heated up to 250° C. within 30 minutes and maintained for 2 h. After cooled down to room temperature within 20 minutes, the mixture was taken out of the reactor and the liquid product was separated from the solid catalyst by filtration. Results based on GC analysis show that 80% of methyl oleate was isomerized. The product composition is shown in Table 1.

TABLE 1

| Example | <=$C_{10}$ | i-$C_{12}$ | $C_{12}$ | i-$C_{14}$ | $C_{14}^1$ | $C_{14}$ | i-$C_{16}$ | $C_{16}^1$ | $C_{16}$ | i-$C_{18}$ | $C_{18}^1$ | $C_{18}$ | other |
|---|---|---|---|---|---|---|---|---|---|---|---|---|---|
| Feed | 0.83 | 0.38 | 0 | 0.21 | 0.54 | 2.4 | 0.94 | 5.46 | 4.82 | 1.84 | 75.93 | 1.55 | 5.1 |
| 1 | 0.26 | 0.42 | 1.55 | 0.62 | 0.00 | 2.41 | 4.61 | 0.96 | 6.50 | 51.23 | 15.41 | 4.23 | 11.80 |

EXAMPLE 2

In a high throughput batch reactor system, five catalysts were tested. Catalysts 2, 4 and 5 represent the technology of the present invention, while examples 1 and 3 are not metal exchanged catalysts. In each reactor, 0.05 g of catalyst and 1 g of methyl oleate were loaded. After sealed, the reactor system was purged with nitrogen. A nitrogen pressure of 100 psig was approached at room temperature. With an active stirring, the mixture of methyl oleate and the catalyst was heated up to 250° C. within 30 minutes and maintained for 7 h. After cooled down to room temperature within 20 minutes, the mixture was taken out of the reactor and the liquid product was separated from the solid catalyst by filtration. Table 2 lists these five catalysts. GC results are in Table 3. Metal exchanged zeolites gave higher yield of branched products.

TABLE 2

| Catalyst # | Name |
|---|---|
| 1 (comparative) | HBeta(TRICAT) |
| 2 | Cu-Beta(aqueous ion-exchange) |
| 3 (comparative) | HBeta(TOSOH) |
| 4 | Cu-Beta (aqueous ion-exchange) |
| 5 | Cu-Beta (solid state ion-exchange) |

TABLE 3

| Catalyst # | $\leq C_{10}$ | $i\text{-}C_{12}$ | $C_{12}$ | $i\text{-}C_{14}$ | $C_{14}^1$ | $C_{14}$ | $i\text{-}C_{16}$ | $C_{16}^1$ | $C_{16}$ | $i\text{-}C_{18}$ | $C_{18}^1$ | $C_{18}$ | other |
|---|---|---|---|---|---|---|---|---|---|---|---|---|---|
| 1 | 0.04 | 0.14 | 3.09 | 0.44 | 0.00 | 1.63 | 4.41 | 0.69 | 6.53 | 48.20 | 15.97 | 3.87 | 14.99 |
| 2 | 0.02 | 0.3 | 3.09 | 1.22 | 0 | 2.88 | 7.55 | 1.62 | 8.42 | 55.62 | 7.34 | 3.97 | 7.97 |
| 3 | 0.06 | 0.16 | 2.84 | 0.52 | 0.05 | 2.02 | 3.93 | 0.96 | 6.04 | 43.45 | 24.49 | 3.23 | 12.25 |
| 4 | 0.37 | 0.43 | 3.21 | 1.5 | 0 | 3.57 | 12.64 | 2.61 | 10.52 | 49.29 | 4.99 | 5.23 | 5.64 |
| 5 | 0.01 | 0.23 | 3.6 | 0.37 | 0 | 2.7 | 7.18 | 1.52 | 7.95 | 57.76 | 7.61 | 3.51 | 7.56 |

EXAMPLE 3

Figure 1:
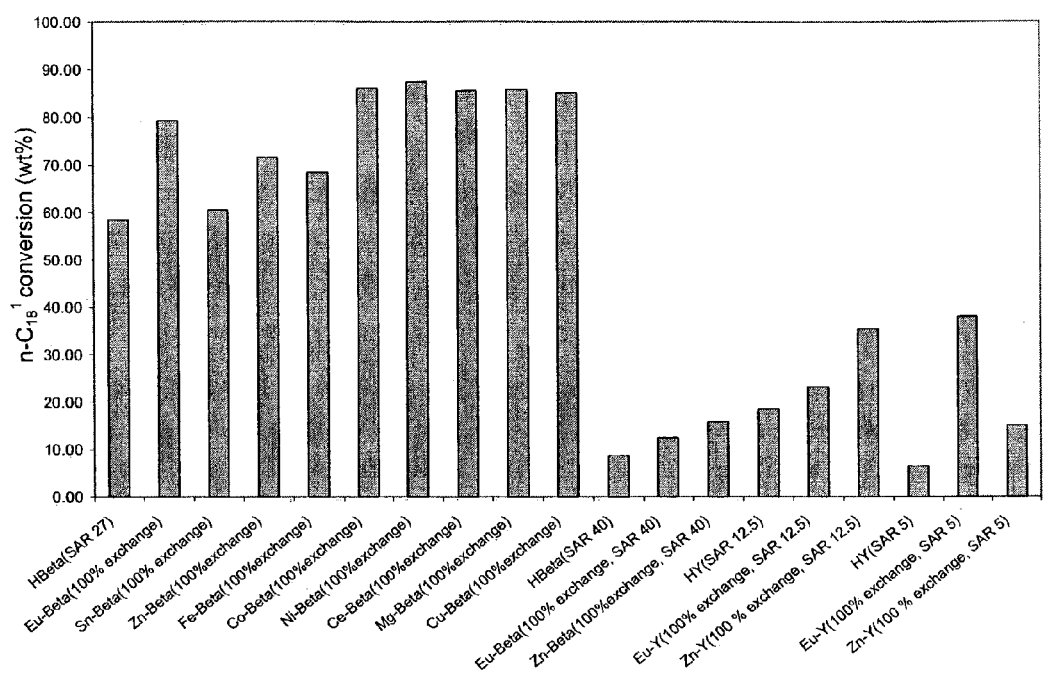

In a high throughput batch reactor, 19 catalysts were tested under the same conditions: 250° C., 100 psig $N_2$ (initial), 7 h for oleic acid isomerization. These catalysts include Beta (SAR 27), Beta (SAR 40), Y(SAR 12.5) and Y (SAR 5) with different cations. Proton form ($H^+$) zeolites were obtained by calcining $NH_4^+$ form zeolite (comparative sample). The ion-exchange started from $NH_4^+$ form zeolites. All catalysts were in powder form. FIG. 1 illustrates the markedly increased activity due to the inclusion of metal ions. The metal ions include alkaline earth ions, transition metal ions, rare earth metal ions, group IB and IIB metal ions. All exchanged metal ions showed improvement over proton form zeolites. See FIG. 1.

EXAMPLE 4

In a high throughput batch reactor, 5 catalysts were tested under same conditions: 250° C., 100 psig $N_2$ (initial), 7 h for oleic acid isomerization. These catalysts include Beta (SAR 27) with different cations. FIG. 2 illustrates the reaction results. The metal ions in this batch include additional transition metal ions and post transition metal ions.

EXAMPLE 5

In a test conducted in the high throughput reactor, the activities of two Beta samples, which were ion-exchanged with $Eu^{3+}$ to different degrees (50% and 100%, respectively, theoretical values), were compared. Table 4 shows the results. Both showed improved performance over the proton form zeolite.

TABLE 4

Beta zeolites with different degree of $Eu^{3+}$ exchange

| Catalyst | $n\text{-}C_{18}^1$ conversion (wt %) |
|---|---|
| Eu-HBeta(50% exchange) | 69.0 |
| Eu-Beta(100% exchange) | 71.9 |

EXAMPLE 6

In a conventional autoclave batch reactor (135 ml), three Beta catalysts with different cations were tested under the same conditions: 250° C., 50 psig $N_2$ (initial), 7 h for oleic acid isomerization under agitation. The results are shown in Table 5. The HBeta zeolite is used as a comparative sample.

TABLE 5

Beta zeolites exchanged with different cations

| Catalyst | $n\text{-}C_{18}^1$ conversion (wt %) |
|---|---|
| HBeta (SAR 27) | 57.0 |
| Zn-Beta(100% exchange) | 69.2 |
| Cu-Beta(100% exchange) | 82.8 |

An elemental analysis showed that the reaction product from Zn-Beta catalyst contained about 2.5–5 ppm Zn. Therefore, it is considered that no leaching of cation occurred during the reaction.

EXAMPLE 7

In support of composition of matter claims directed to the branched fatty acids of the invention, the inventors analyzed the branched products with the GC and compared the results to three commercial samples of branched acids. According to this analytical method GC peaks of mono-, di-, and multi-branched products are able to be resolved into separate groups so that the relative amount of these three groups of branched products could be compared quantitatively.

Figure 3:
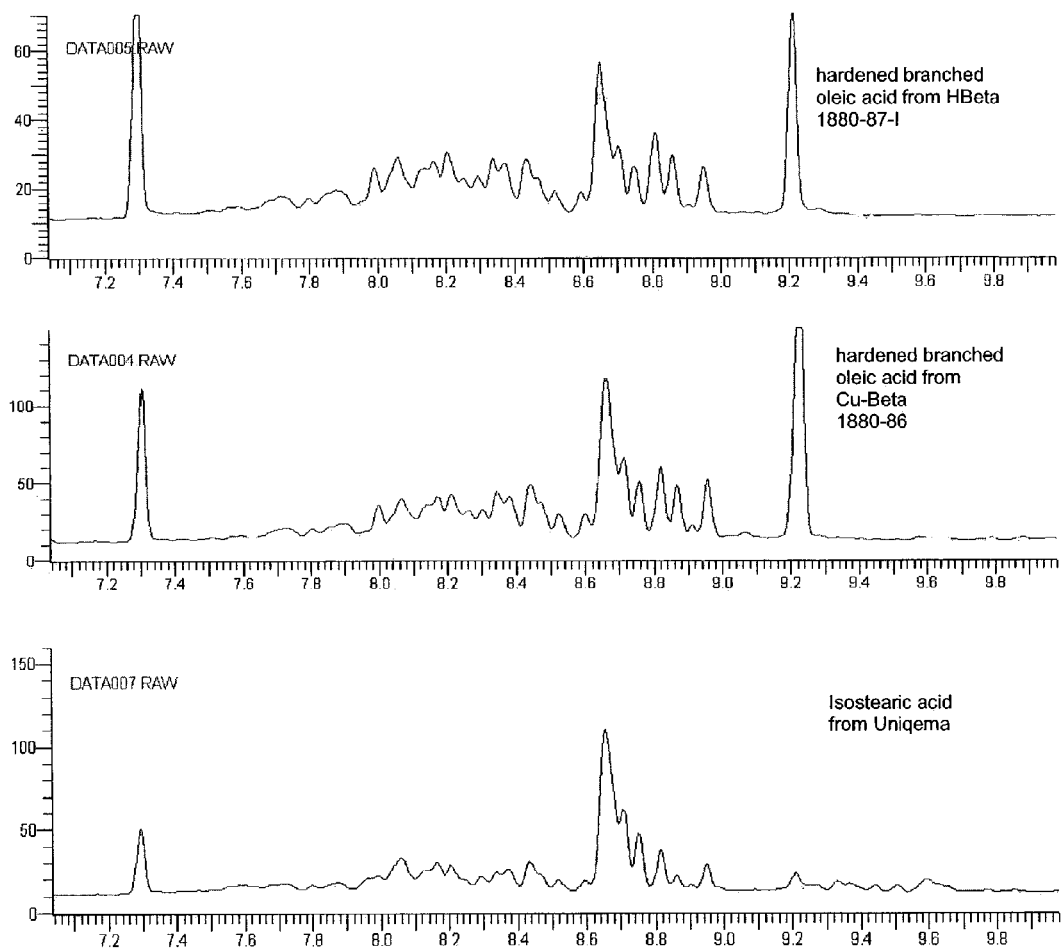
Figure 4:
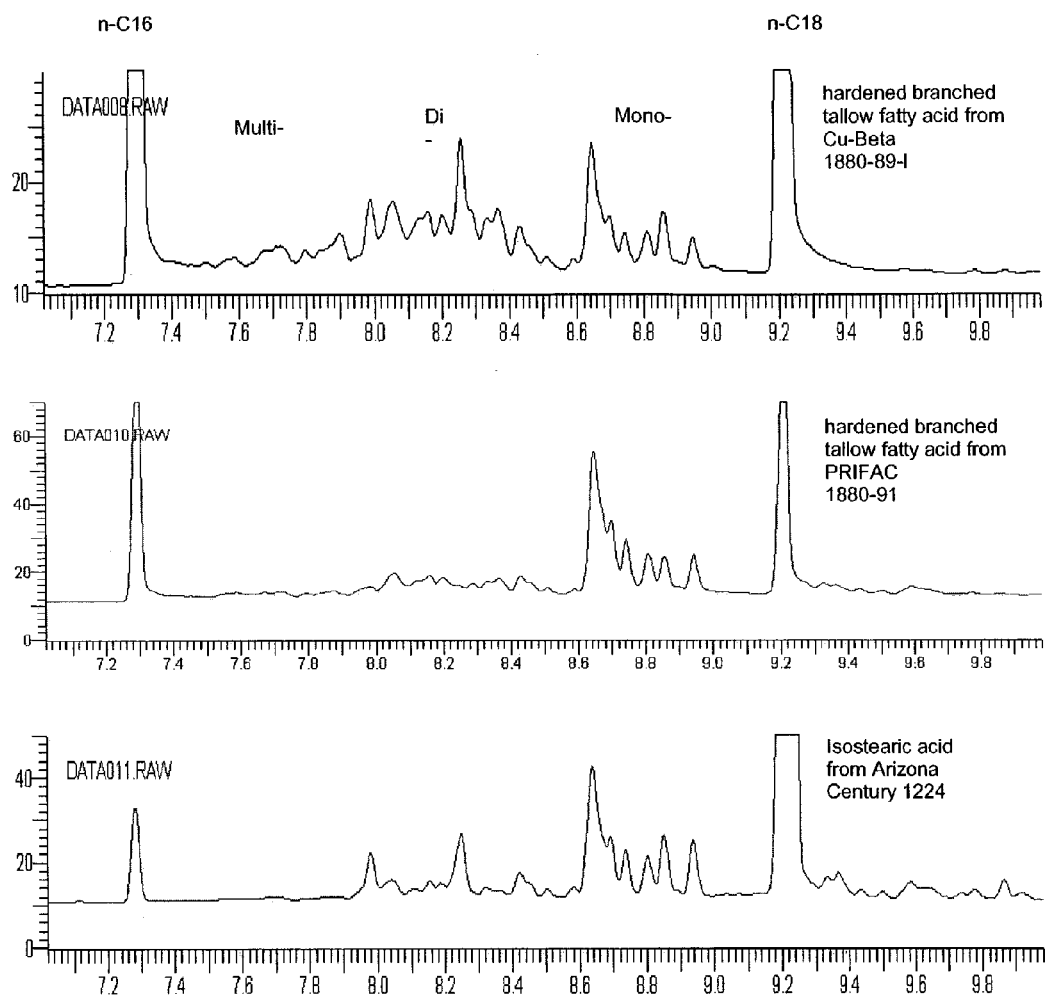
Figure 5:
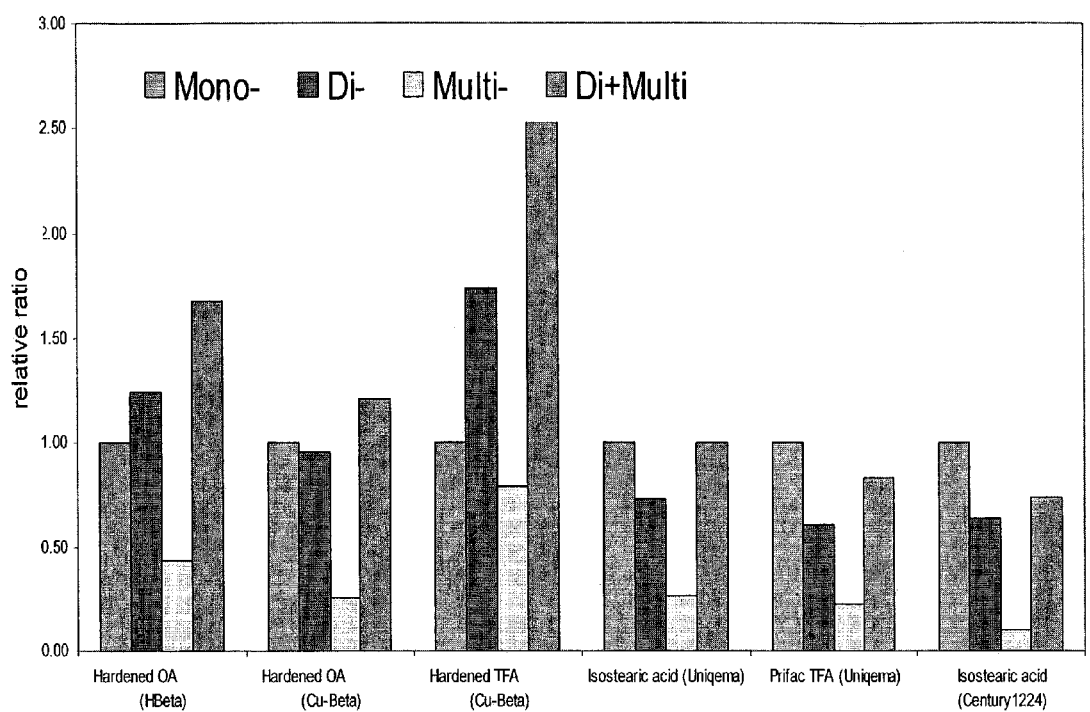

Three products prepared in accordance with the present invention were compared to three commercial isostearic acid products. All products, including the commercial ones, were fully saturated prior to GC analysis so that direct comparison can be made. The results are found below and in FIGS. 3–5.

|  | Hardened OA H-Beta | Hardened OA Cu-Beta | Hard TFA Cu-Beta | Isostearic Acid (Uniqema) | Prifac TFA (Uniqema) | Isostearic Acid (Century 1224) |
| --- | --- | --- | --- | --- | --- | --- |
| Mono- | 1.00 | 1.00 | 1.00 | 1.00 | 1.00 | 1.00 |
| Di- | 1.24 | 0.96 | 1.74 | 0.73 | 0.60 | 0.64 |
| Multi- | 0.44 | 0.25 | 0.79 | 0.26 | 0.23 | 0.10 |
| Di(+) | 1.68 | 1.21 | 2.54 | 1.0 | 0.83 | 0.74 |

The total of mono-branched fatty acids is used as a reference in all samples, set as area unit of 1.00. The second row shows the relative amount of di-branched fatty acids, the third row of multi-branched fatty acids, and the fourth the total of di- and multi-branched fatty acids. The integration of C18 fractions is employed to illustrate the differences.

In the di-branched isomers, all commercial products fall below 0.75 (0.73 according to the table), i.e. di-/mono-ratio of 0.75, while products prepared in accordance with the process/catalyst of the present invention have di-/mono-ratio of above 0.95. The ratio of total (Di-+multi-) branched/mono-branched in the commercial products is 1, the ratios of the present invention is above 1.20.

We claim:

1. A process for the isomerization of a feedstock which comprises unsaturated linear fatty acids, alkyl esters of unsaturated fatty acids or mixtures thereof, wherein said process comprises subjecting said feedstock to an isomerization reaction in the presence of at least one metal ion exchanged acidic catalyst which comprises at least one non-zero valent metal ion.

2. The process of claim 1 wherein said non-zero valent metal ion is selected from the group consisting of monovalent metal, divalent metal, trivalent metal, tetravalent metal, pentavalent metal, hexavalent metal and mixtures thereof.

3. The process of claim 2 wherein said higher valent metal is selected from the group consisting of $Li^+$, $Cu^+$, $Rh^+$, $Ir^+$, $Mg^{2+}$, $Ca^{2+}$, $Mn^{2+}$, $Fe^{2+}$, $Co^{2+}$, $Ni^{2+}$, $Cu^{2+}$, $Zn^{2+}$, $Sr^{2+}$, $Mo^{2+}$, $Pd^{2+}$, $Sn^{2+}$, $Ce^{2+}$, $Pt^{2+}$, $Sc^{3+}$, $Cr^{3+}$, $Fe^{3+}$, $Co^{3+}$, $Ga^{3+}$, $Y^{3+}$, $Nb^{3+}$, $Ru^{3+}$, $Rh^{3+}$, $La^{3+}$, $Ln^{3+}$, $Ce^{3+}$, $Pr^{3+}$, $Nd^{3+}$, $Pm^{3+}$, $Sm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Ir^{3+}$, $Bi^{3+}$, $Ti^{4+}$, $Mn^{4+}$, $Zr^{4+}$, $Mo^{4+}$, $Sn^{4+}$, $Ce^{4+}$, $V^{5+}$, $Nb^{5+}$, $Mo^{6+}$, and mixtures thereof.

4. The process of claim 1 wherein the metal ion concentration is at least 0.001% of the exchange capacity of the catalyst support.

5. The process of claim 1 wherein the metal ion concentration is at least 0.5% of the exchange capacity.

6. The process of claim 5 wherein the metal ion concentration is at least 1% of the exchange capacity.

7. The process of claim 6 wherein the metal ion concentration is at least 2% of the exchange capacity.

8. The process of claim 7 wherein the metal ion concentration is in the range of 0.001 to above 200% exchange level.

9. The process of claim 8 wherein the metal ion concentration is in the range of 0.5 to 100% exchange level.

10. The process of claim 9 wherein the metal ion concentration is in the range of 1 to 50% exchange level.

11. The process of claim 1 wherein the isomerization of said feedstock comprises branching of the fatty acids or alkyl esters thereof.

12. The process of claim 1 wherein said acidic catalyst comprises a zeolite, acidic clay, molecular sieve, or mixtures thereof.

13. The process of claim 12 wherein said acidic catalyst comprises a zeolite.

14. The process of claim 12 wherein said zeolite comprises at least one of the following framework structures: AEL, AFO, AHT, BOG, CGF, CGS, CON, DFO, FAU, FER, HEU, AFS, AFY, BEA, BPH, CLO, EMT, FAU, GME, MOR, MFI, or mixtures thereof.

15. The process of claim 12 wherein the $SiO_2/Al_2O_3$ ratio of the zeolite is at least 5.

16. The process according to claim 1 wherein the feedstock comprises of at least 50% by weight of unsaturated fatty acids, alkyl esters of unsaturated fatty acids or mixtures thereof.

17. The process of claim 16 wherein the feedstock comprises of at least 70% by weight oleic acid.

18. The process claim 1 wherein at least part of the isomerization is performed at a temperature of between 100° C. and 350° C.

19. The process of claim 18 wherein at least part of the isomerization is carried out at a temperature of between 230° C. and 285° C.

20. The process of claim 18 wherein the amount of catalyst used is between 0.01 and 20% by weight of the feedstock in the batch reactor.

21. An unsaturated, branched fatty acid or alkyl ester thereof prepared by isomerizing a feedstock which comprises unsaturated linear fatty acids, alkyl esters of unsaturated fatty acids or mixtures thereof, wherein said process comprises subjecting said feedstock to an isomerization reaction in the presence of at least one metal ion exchanged acidic catalyst which comprises at least one higher valent metal.

22. The branched fatty acid or alkyl ester thereof of claim 21 wherein said higher valent metal is selected from the group consisting of monovalent metal, divalent metal, trivalent metal, tetravalent metal, pentavalent metal, hexavalent metal and mixtures thereof.

23. The branched fatty acid or alkyl ester thereof of claim 22 wherein said higher valent metal is selected from the group consisting of $Li^+$, $Cu^+$, $Rh^+$, $Ir^+$, $Mg^{2+}$, $Ca^{2+}$, $Mn^{2+}$, $Fe^{2+}$, $Co^{2+}$, $Ni^{2+}$, $Cu^{2+}$, $Zn^{2+}$, $Sr^{2+}$, $Mo^{2+}$, $Pd^{2+}$, $Sn^{2+}$, $Ce^{2+}$, $Pt^{2+}$, $Sc^{3+}$, $Cr^{3+}$, $Fe^{3+}$, $Co^{3+}$, $Ga^{3+}$, $Y^{3+}$, $Nb^{3+}$, $Ru^{3+}$, $Rh^{3+}$, $La^{3+}$, $Ln^{3+}$, $Ce^{3+}$, $Pr^{3+}$, $Nd^{3+}$, $Pm^{3+}$, $Sm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Ir^{3+}$, $Bi^{3+}$, $Ti^{4+}$, $Mn^{4+}$, $Zr^{4+}$, $Mo^{4+}$, $Sn^{4+}$, $Ce^{4+}$, $V^{5+}$, $Nb^{5+}$, $Mo^{6+}$, and mixtures thereof.

24. The branched fatty acid or alkyl ester thereof of claim 21 wherein said acidic catalyst comprises a zeolite, acidic clay, molecular sieve, or mixtures thereof.

25. The branched fatty acid or alkyl ester thereof of claim 24 wherein said acidic catalyst comprises a zeolite.

26. The branched fatty acid or alkyl ester thereof of claim 25 wherein said zeolite comprises at least one of the following framework structures: CON, DFO, FAU, AFS, AFY, BEA, BPH, EMT, GME, MOR, or mixtures thereof.

27. The branched fatty acid or alkyl ester thereof of claim 25 wherein the $SiO_2/Al_2O_3$ ratio of the zeolite is at least 5.

28. The branched fatty acid or alkyl ester thereof according to claim 21 wherein the feedstock comprises of at least 50% by weight of unsaturated fatty acids, alkyl esters of unsaturated fatty acids or mixtures thereof.

29. The branched fatty acid or alkyl ester thereof claim 21 wherein at least part of the isomerization is performed at a temperature of between 100° C. and 350° C.

30. The branched fatty acid or alkyl ester thereof of claim 21 wherein the amount of catalyst used is between 0.01 and 20% by weight of the feedstock in the batch reactor.

31. A derivative prepared from the branched fatty acid or alkyl ester thereof of claim 25 wherein said derivative is selected from the group consisting of amphoteric, non-ionic, anionic and cationic surfactants.

32. The derivative of claim 31 wherein said derivative is selected from the group consisting of fatty acid glucamides, glycerol esters, polyhydric esters, sulfoesters, sucrose esters, alpha sulfonates, N-acyl sarcosinates, acylated protein hydrolysates, acyl isethionates, amido propyl amine and derivatives thereof, alkanolamide, ethoxylated alkanolamides, nitriles, N-aryl taurates, soaps, esteramines, esterquats, alkyl polyglycosides (APGs), alcohol sulfates, phosphate esters, polyalkoxycarbonates and mixtures thereof.

33. An unsaturated, branched fatty acid or alkyl ester thereof prepared by isomerizing a feedstock which comprises unsaturated linear fatty acids, alkyl esters of unsaturated fatty acids or mixtures thereof, wherein the di-branching:mono-branching ratio of branched fatty acid or alkyl ester thereof is greater than 0.75.

34. The branched fatty acid or alkyl ester thereof of claim 33 wherein the di-branching:mono-branching ratio of branched fatty acid or alkyl ester thereof is greater than 0.80.

35. The branched fatty acid or alkyl ester thereof of claim 33 wherein the di-branching:mono-branching ratio of branched fatty acid or alkyl ester thereof is greater than 0.90.

36. The branched fatty acid or alkyl ester thereof of claim 33 wherein the di-branching:mono-branching ratio of branched fatty acid or alkyl ester thereof is greater than 1.0.

37. The branched fatty acid or alkyl ester thereof of claim 33 wherein the di-branching:mono-branching ratio of branched fatty acid or alkyl ester thereof is in the range of from greater than 0.75 to 3.0.

38. The branched fatty acid or alkyl ester thereof of claim 33 wherein the total (Di-+multi-) branched:mono-branched ratio is greater than 1.20.

* * * * *